United States Patent [19]
Heberle-Bors et al.

[11] Patent Number: 5,840,557
[45] Date of Patent: Nov. 24, 1998

[54] METHOD FOR PRODUCING SEEDS AND PLANTS THEREOF INVOLVING AN IN VITRO STEP

[75] Inventors: Erwin Heberle-Bors, Vienna, Austria; Rosa Maria Benito Moreno, Valenzia, Spain; Anna Alwen, Cairo, Egypt; Alisher Tourajew, Vienna; Eva Maria Stöger, Salzburg, both of Austria

[73] Assignee: Mogen International nv, Leiden, Netherlands

[21] Appl. No.: 826,331

[22] Filed: Mar. 27, 1997

Related U.S. Application Data

[63] Continuation of Ser. No. 491,720, Jun. 19, 1995, abandoned, which is a continuation-in-part of Ser. No. 228,357, Apr. 15, 1994, abandoned, which is a continuation-in-part of Ser. No. 458,685, Jan. 12, 1990, abandoned.

[30] Foreign Application Priority Data

Jul. 21, 1987 [DE] Germany .......................... 37 24 154.0

[51] Int. Cl.$^6$ .......................... C12N 15/00; C12N 15/29; C12N 15/82; A01H 14/00
[52] U.S. Cl. .................................. 435/172.3; 435/320.1; 435/419; 800/205; 800/200; 800/250
[58] Field of Search .............................. 435/172.3, 320.1, 435/419; 800/200, 205, 250

[56] References Cited

FOREIGN PATENT DOCUMENTS 0 270 356  8/1988  European Pat. Off. ........ C12N 15/00

OTHER PUBLICATIONS

Negrutiu et al. Attempts to Transform for Kanamycin–Resistance in Mature Pollen of Tobacco. Biotechno. Ecol. Pollen, Proc. Int. Conf., Meeting Date 1985, Mulcahy et al., eds., 1986, Springer: New York.

Tanaka et al. Studies on Microspore Development in Liliaceous Plants III. Pollen Tube Development in Lily Pollins Cultured from the Uninucleate Microspore Stage. Plant and Cell Physiol. 22(1), 149–153, 1981.

Yasuo Ohta. High–efficiency genetic transformation of maize by a mixture of pollen and exogenous DNA. Proc. Natl. Acad. Sci. USA, vol. 83, pp. 715–719, Feb. 1986.

I. Potrykus, "Gene Transfer to Plants: Assessment of Published Approaches and Results", Annu. Rev. Plant Physiol. Plant Mol. Biol. 1991, 42: pp. 205–225.

Foster et al. "Comparative Morphology of Vascular Plants", 2nd Edition, San Francisco, W.H. Freeman et al., 1974, pp. 664–651.

Zambryski et al., "Ti Plasmid Vector for the Introduction of DNA Into Plant Cells Without Alteration of Their Normal Regeneration Capacity", The EMBO Journal vol. 2 No. 12, pp. 2143–2150 (1983).

E. Stoger et al., "Comparison of Different Techniques for Gene Transfer Into Mature and Immature Tobacco Pollen", Transgenic Research, vol. 1 (92) pp. 71–78.

*Primary Examiner*—Douglas W. Robinson
*Assistant Examiner*—Thomas Haas
*Attorney, Agent, or Firm*—Wenderoth, Lind & Ponack, L.L.P.

[57] ABSTRACT

A method for producing transgenic seeds and plants, which comprises isolating, from anthers, microspores in their uninucleate stage and removing tissue in which they are embedded, culturing the isolated microspores in a nutrient solution, transferring foreign genetic material into the isolated microspores to obtain transformed microspores, bringing about complete maturation of the transformed microspores to obtain transformed pollen grains in vitro, pollinating receiver plants with the transformed pollen grains and obtaining seeds from the pollinated receiver plants.

19 Claims, No Drawings

METHOD FOR PRODUCING SEEDS AND PLANTS THEREOF INVOLVING AN IN VITRO STEP

This application is a continuation of now abandoned Ser. No. 08/491,720, filed Jun. 19, 1995, which is a continuation-in-part of now abandoned Ser. No. 08/228,357 filed Apr. 15, 1994, which is a continuation-in-part of now abandoned Ser. No. 07/458,685 filed Jan. 12, 1990.

BACKGROUND OF THE INVENTION

1. Field of the Invention

The invention relates to a method for producing seeds and plants thereof by culturing isolated, immature pollen grains in vitro, producing seeds by natural pollination in vivo and fertilization of the seeds derived from pollination and culturing plants therefrom in vivo. This method is useful for the control of self-incompatibility, cytoplasmic male sterility and pollen-allergen formation. Additionally it offers an alternative route for transferring foreign genes into plants which cannot be regenerated in vivo by transferring foreign DNA into the immature pollen grains.

2. Description of the Related Art

Various techniques for gene transfer into plants are already available. Each has its advantages and disadvantages. (See Goodman et al., Science, Vol. 236, pages 48–53 (1987). *Agrobacterium tumefaciens* is the most common vector nowadays. However, it is restricted to certain host strains. The use of *A. tumefaciens* as a vector still depend on the regeneration of in vitro- cultured somatic cells to produce transgenic plants which are capable of forming transgenic progeny. Direct gene transfer by electroporation, liposomes, microinjection and other physical-chemical methods largely depends on the use of protoplasts as target cells. However, regeneration from protoplasts is difficult and has not even been achieved in many species.

A different target cell has been suggested as an alternative to these gene transfer methods, the pollen grain. According to D. Hess, Plenum Press, New York, 519–537 (1975), it is possible for the mature pollen to take up foreign DNA and to transfer this foreign DNA to the egg cell, as a "supervector", by means of natural pollination and fertilization. Similarly, X-ray treated pollen is said to be capable of transporting fragments of irradiated genome into the egg cell. See Pandey, Nature, Vol. 256, pages 310–313 (1975). DeWet (WO 85/01856) reports that maize pollen which has been treated with exogenous DNA takes up this DNA on germination and transports it into the egg cell after pollination.

In spite of the potentially great importance of gene transfer into, and by, pollen, other laboratories have so far not succeeded in reproducing the results of Hess, Pandey and DeWet. Thus, for example, Engvild, Theor. Appl. Genet, Vol. 69, pages 457–461 (1985) was not able to reproduce Pandey's experiments. In the experiments by Hess (1975) and by DeWet, the uptake of exogenous DNA into-the pollen grain and the genetic and molecular proof of the transferred DNA is the critical link in the chain of reasoning. Proof by phenotype and physiological proof are not sufficient. See Hess, Genetic Manipulation in Plant Breeding, de Gruyter, Berlin, New York, pages 803–811 (1986). The experiments by Sandford et al., Biotechnology and Ecology of Pollen (Mulcahy D, ed.), Springer, Heidelberg, New York, pages 71–75 (1968) also showed that co-culture of mature *Nicotiana langsdorfii* pollen with agrobacteria did not lead to gene transfer into pollen. In a large number of experiments, Negrutiu, Heberle-Bors and Potrykus (loc. cit. 65–70, 1986) did not succeed in transferring the neomycinphosphotransferase gene, which entails resistance to kanamycin, into mature pollen. See Shillito et al., Biotechnology, Vol. 3, pages 1099–1103 (1985). Thus, it was not possible to confirm the statements of Hess and DeWet by means of methods corresponding to the recent state of the art. The fact that the results of Hess and DeWet are not reproducible can be explained by the mature pollen grains immediately starting the formation of a pollen tube as soon as they are put into an aqueous medium, which is required for the gene transfer. Obviously they are no longer fertile at this stage, or the period of time which is available for gene transfer is too short.

In Planta, Vol. 170, pages 141–143 (1987), Pareddy et al. describe the culturing and maturation of immature maize tassels (male inflorescences) in vitro. Pollination was carried out using the isolated mature pollen, and seeds were obtained from the pollinated plants. No proof, by means of genetic markers, for successful fertilization could be furnished.

Tanaka et al., Plant & Cell Physiol., Vol. 22(1), pages 1 and 153 (1981) describe an attempt for producing seeds from immature pollen which was matured in vitro. This attempt however has not been successful.

Surprisingly, it has been found that it is possible to culture immature pollen grains without the natural nutrient tissue containing them, and that, with the mature pollen grains during various stages of maturation, plants can be pollinated and fertilized to bring about normal seed formation, germination and propagation.

SUMMARY OF THE INVENTION

The present invention thus relates to a method for producing seeds and plants thereof involving an in vitro step which comprises
  a) isolating, from anthers, immature pollen grains in nutrient solution and removing the tissue in which they are embedded,
  b) culturing the isolated, immature pollen grains in a nutrient solution
  c) bringing about complete maturation of the transformed pollen grains in vitro
  d) pollinating receiver plants with the transformed pollen grains and obtaining seeds from the former.

DESCRIPTION OF THE PREFERRED EMBODIMENTS

A completely novel strategy of gene transfer into plants is made available by the gene transfer into isolated, immature pollen grains, in vitro maturation and the use of pollen as universal "supervector". Compared with other methods, it is considerably simplified because the cell culture phase is reduced to a large extent and the regeneration, which is accompanied by the troublesome phenomenon of somaclonal variation, is omitted. Using this novel method, it is also possible to transform plants which were inaccessible to date to successful gene transfer: thus, for example, many species of cereals, leguminosae and trees cannot be regenerated from single cells or protoplasts.

The potential benefit from gene transfer technology has large economic, ecological and social value. The aim is to alter plants genetically such that yield is increased, that the plants become resistant to diseases and pests, that they become tolerant to cold, heat, drought, salinification and lack of nutrients, that they have better nutritional qualities, that they produce novel raw materials for industry, or that they fix their own nitrogen or become independent of fertilizers in another manner.

It is essential for the invention that pollen grains are cultured without the tissue containing them, i.e. isolated, so that the genetic material to be transferred, coupled to a vector or naked, has direct contact with the pollen grain. If the complete male inflorescence is cultured, it is not possible to transfer genes into the pollen grains with the aid of customary transfer methods (*A. tumefaciens,* electroporation, microinjection and the like) due to obstruction by the extensive surrounding tissue.

Another essential feature of the invention is the use of immature pollen grains. Due to this, the complete period of in vitro maturation is available for gene transfer. Transfer into the immature pollen grain can be carried out in different stages of maturity, depending on the plant species. It is important that the genetic material has to pass through as few cell walls as possible to enter the genome of the sperm nuclei and become part of the zygotic genome on fertilization, in particular when vectors are used for gene transfer. Transfer is preferably carried out when the micropores are in their uninucleate stage, but it can also be carried out during the first pollen mitosis, in the early binucleate stage, as long as the generative cell is still attached to the pollen wall, or alternatively, in those plants whose pollen is trinucleate in the mature stage (cereals), in the stage shortly before or during the second pollen mitosis.

Specifically, the method is carried out as described below, tobacco (*Nicotian tabacum*) being used as a model system. The system can be applied to all plants which can be propagated by pollination in particular to mono- and dicotyledon crop plants, such as wheat, maize, rice, leguminosae, oil crops, vegetable plants, fruit plants and forest plants.

In a preliminary experiment, the development stage of the pollen of the desired plant is determined in a customary manner by isolation of one anther, preparation of a squash and observation under the microscope after the addition of, for example, acetocarmine.

When the pollen has reached the desired stage, the pollen grains are isolated under sterile conditions by squeezing them out of the anthers in a nutrient medium, passing them through a sieve, washing them, collecting them by centrifugation and resuspending them.

Cell density should be higher for pollen grains in an earlier development stage than for pollen grains in a later development stage. For tobacco, cell density of binucleate pollen grains is about $10^5$/ml, and about twice as much in the case of uninucleate microspores.

The nutrient medium used contains all the nutrients and growth substances essential for culturing and maintaining the ability to mature of the pollen grains. Depending on the plant, various compositions can thereby fulfill the function of the nutrient tissue (tapetum). Here, the main constituents of the nutrient medium are sugars, nutrient substances, mineral salts and vitamins, the pH being about 6.5 to 7.5.

In the case of uninucleate microspores, culturing up to the binucleate stage is carried out in a medium considerably enriched with sugar, for example sucrose (at least 0.25 mol/l), and further nutrient substances. For example, the additional nutrient substances may be added in the form of coconut water or lactalbumin hydrolysate. When the pollen grains have reached the binucleate stage, they can be transferred to a medium less rich in nutrients.

When the in vitro maturation is complete, the pollen grains are harvested for pollination. For this purpose, they are centrifuged off, washed, and, for pollination, applied to flowers from which the anthers have previously been removed, either in an aqueous medium or dried. Seeds which are capable of germination are obtained in a generally customary manner from the plants pollinated with in vitro-matured pollen grains.

For gene transfer during in vitro culturing, the foreign genetic material to be transferred can be introduced into the pollen grains either using a customary vector, such as, for example, *A. tumefaciens,* or as naked DNA by direct transfer by means of a DNA gun, electroporation, micro-injection or other physicochemical methods. The expression "foreign genetic material" denotes any genetic material produced outside the pollen grain to be transformed.

When maturation is complete, the pollen grains are harvested in the above-mentioned manner for pollination.

As proof of successful in vitro maturation, pollen grains of a tobacco plant having 2 marker genes ($KAN^R$, NOS) were matured in vitro, and normal wild-type plants were pollinated without these pollen grains. The seeds obtained were sterilized and germinated in a kanamycin-containing germination medium. Mendelian segregation of the marker genes was confirmed by counting the seedlings in the selective medium. Seedlings which had been germinated on kanamycin-free medium, also showed Mendelian segregation of the NOS gene following nopaline detection by high-frequency paper electrophoresis.

This proves that it was the in vitro-matured pollen grains which carried out fertilization and not any contaminating pollen from other plants.

As proof for the expression of the foreign gene introduced by transformation during in vitro culturing, the chloramphenicolacetyltransferase activity (CAT activity) was detected in an enzyme assay in a homogenate prepared from the transformed pollen grains.

In addition to the CAT gene, a cytochemically-detectable gene, the beta glucuronidase gene (GUS gene) was also used. In this experiment, the agrobacteria were co-cultured with the pollen and then removed or destroyed by daily washing with the antibiotic claforan. In a cytochemical assay (staining blue of the pollen) it was possible to detect more than 50% blue, in vitro-matured pollen. Non-infected pollen, or pollen which had been infected with agrobacteria with, or without a non-functional GUS gene, did not show blue staining on addition of the substrate. A fluorimetrical assay showed high GUS activity in GUS-transformed pollen, and also in pollen from GUS-transformed plants which served as a positive control. Pollen which had not been infected, or which had been infected with agrobacteria free of the GUS gene, did not show GUS activity. Infection with agrobacteria without infection genes but with a complete GUS gene in the T-DNA likewise did not result in any GUS activity in the pollen (cytochemically as well as fluorimetrically).

This leads to the conclusion that gene transfer into the pollen was carried out by *Agrobacterium tumefaciens.* Successful gene transfer into the pollen is furthermore suggested by the visible adhesion of the agrobacteria to the pollen surface with formation of cellulose fibrils (electron microscope photos).

EXAMPLE 1

Determination of the Stage of Pollen Development

Tobacco flowers of various lengths were harvested, the anthers were isolated under sterile conditions, one of the five anthers were transferred to a slide together with a drop of acetocarmine (4% of carmine in 45% strength acetic acid), and a squash was prepared. The development stage of the pollen grains was determined under the microscope after half an hour.

EXAMPLE 2

Isolation of the Pollen Grains

The tobacco pollen grains were isolated by squashing the anthers carefully with a glass rod and a microscopy mortar in AMGLU medium (1), under sterile conditions, passing the resulting pollen suspension through a 75 µm sieve and washing the pollen suspension twice with AMGLU medium. Finally, the pollen suspension was collected by centrifugation in an Eppendorf centrifuge at 6,500 rpm.

EXAMPLE 3

Pollen Culture for the Maturation of Early-Binucleate pollen grains

Early binucleate tobacco pollen grains were isolated and the cell density in AMGLU medium was adjusted to $10^5$/ml. One ml of the pollen suspension was cultured in 35 mm Petri dishes at 25° C. in the dark. Depending on the exact development stage of the pollen grains, they had matured after 2 to 5 days and could be harvested.

EXAMPLE 4

Pollen Culture For the Maturation of Uninucleate Microspores

Uninucleate tobacco microspores were cultured in MR24 medium (2) at a cell density of $2\times10^5$/ml. As soon as the pollen grains had reached the binucleate stage (after 2 to 5 days, depending on the exact age), they were collected by centrifugation and cultured further in M1S medium (3) until maturation was complete.

Alternatively, very good results were obtained when MR26 medium (2') was used for culturing. As soon as the pollen grains had reached the binucleate stage (after 3 days), the same volume of M2S medium was added. After a further day, the pollen grains were collected by centrifugation and cultured further in M2S medium (3') at a cell density of $10^5$/ml until maturation was complete (one day).

EXAMPLE 5

Pollination and Proof of Fertilization

The tobacco pollen grains were collected by centrifugation and washed in BK medium (Brewbaker and Kwack 1963), and the cell density was adjusted to $1.25\times10^6$/ml. The still closed anthers were removed from flowers which were just about to open (red flower tip). As soon as the flower had opened, a 4 µl-drop of the pollen suspension was applied, with the aid of a 20 µl-pipette, to the stigma of the flower such that the stigma was covered completely in pollen suspension. These operations were carried out under conditions without movement of air and remote from other plants of the same species. As soon as the drop had dried on the stigma, stigma and pistil were covered with a 4 cm piece of straw to prevent cross-fertilization. The plants were then returned to the greenhouse.

EXAMPLE 6

Harvest of the Seeds, Germination of the Seeds and Genetic Assay

As proof that it was the in vitro-matured pollen grains which had carried out the pollination and fertilization, pollen grains of a transgenic plant were matured in vitro and normal wild-type plants were pollinated with these pollen grains. The transgenic plant contained the gene for neomycin-phospho-transferase (resistance to kanamycin) and the nopalinsynthase gene as a marker gene. Self-fertilizations and the reciprocal cross with in vitro-matured wild-type pollen were also carried out.

The mature seed capsules (brown and dry) obtained as in Example 5 were harvested and the seeds were isolated by cutting off the tip of the capsule and transferring the seed grains directly into an Eppendorf tube. The seeds were surface-sterilized for 5 min in an NaOCl solution (3% free chlorine), washed twice with sterile water and placed on a seed germination medium containing kanamycin (4). After four weeks, the number of $Kan^R$ and $Kan^S$ seedlings was counted. In the above crossing experiment, the two reciprocal crosses resulted in segregation of $Kan^R$: $Kan^S$ 1:1. Seedlings grown without kanamycin showed a segregation of Nos+:Nos−=1:1 following a test for nopalin by high-frequency paper electrophoresis. As expected, a 0:1 segregation for both marker genes was observed for self-fertilization with in vitro matured wild types. Self-fertilization with in vitro-matured pollen of the transgenic plant resulted in a 3:1 segregation.

EXAMPLE 7

Transient Expression of the CAT Gene

Agrobacteria (A. tumefaciens without tumor genes, containing the CAT gene coupled to a 35S promoter) were preincubated for one day in Luria broth. Pollen grains in the early binucleate stage were isolated and cultured in AMGLU medium. The bacterial suspension was adjusted to an $OD_{580}$ of 0.2 using AMGLU medium. After a further dilution with AMGLU medium of 1:10, 20 µl of the bacterial suspension were added to 1 ml of the pollen suspension. After 24 hours of co-culturing 1 µl of claforan (1 g/2 ml) per ml was added to destroy the agrobacteria. After a further two days, the pollen grains were harvested and an extract was prepared. For this, 1.5 ml of calcium washing solution (5), pH 5.6, were added per ml of pollen suspension and the mixture was centrifuged for 5 min at 4,000 rpm and washed with a Tris buffer (0.25M, pH 7.8). After centrifugation, 200 µl of Tris buffer were added to the pollen pellet, and homogenization by ultrasound (3×15 sec) was carried out on ice. After 10 min on ice, the mixture was centrifuged and the supernatant was kept at −20° C.

The CAT assay was carried out as described by Sleigh, Anal. Biochem., Vol. 56, pages 251–256 (1986). 30 µl of extract were mixed with 20 µl of chloramphenicol (8 mM), 30 µl of Tris buffer and 20 µl of $^{14}$C-marked acetyl-CoA (5 uCi/ml in 0.5 mM of cold acetyl-CoA). Following incubation for 1 hour at 37° C., the acetylated chloramphenicol was extracted by shaking with ethyl acetate (2×100 µl), and the radioactivity was measured in scintillation counter.

Radioactivity (cpm) in the CAT assay of extracts from tobacco pollen following co-culturing with A. tumefaciens

|  | cpm |
|---|---|
| Pollen in AMGLU medium | 400 |
| Pollen together with agrobacteria in AMGLU medium | 6,000 |
| Pollen together with acetosyringon-activated agrobacteria in AMGLU medium | 6,000 |
| Only agrobacteria in AMGLU medium | 500 |
| Only acetosyringon-activated agrobacteria in AMGLU medium | 500 |

The strong radioactivity signal shows that the agrobacteria have successfully infected the pollen grains and that the T-DNA must have entered the nucleus of the growing cell for expression (transcription).

As a further control to show that the agrobacteria themselves did not have any CAT activity, no CAT activity was detected in an agrobacteria culture in Luria broth over a complete growth cycle.

EXAMPLE 8

Expression of the GUS Gene in Tobacco Pollen

Agrobacteria of the strain LBA 4404 (*A. tumfaciens*, disarmed, having the beta-glucuronidase (GUS) gene, coupled with 35S promoter and terminator, see Matzke and Matzke, Plant Molecular Biology, Vol. 7, pages 357–365 (1986), were pre-incubated for one day in Luria broth. Pollen grains in the late uninucleate stage were isolated and adjusted to an $OD_{580}$ of 0.2 in MR26 medium. Following a further dilution with MR26 medium of 1:10, 20 µl of the bacterial suspension were added to 1 ml of the pollen suspension. After 14–20 hours of co-culturing, the pollen was collected by centrifugation, washed three times with MR 26 medium containing claforan (1 g/2 ml) and cultured further. The medium containing claforan was changed every day until maturation of the pollen. 40 µl of the last medium (M2S, containing claforan) were added to a Luria broth. No bacterial growth was observed.

The mature pollen was collected by centrifugation, and some was taken up in MR26 medium. Following the addition of X-Glu (5-bromo-4-chloro-3-indolyl glucuronide) to a final concentration of 1 mM and incubation for 4–12 hours at 37°; see Jefferson, Plant Molecular Biology Reporter, Vol. 5, No. 4, pages 387–405, (1987), the formation of indigo (product of the beta-glucuronidase from X-Glu) could be detected with the aid of the blue staining of the pollen under a light microscope. More than 50% of the live mature pollen showed blue staining.

A second portion of the co-cultured and in vitro-matured pollen was germinated in GK medium (like BK medium, but twice the concentration of boric acid). GUS activity could also be detected in the pollen tubes of the germinated pollen.

In a control experiment, pollen was infected with a strain of agrobacteria of LBA4404, which, in its T-DNA, contained the GUS gene without the promoter (supplied by Drs. Matzke, Salzburg). After in vitro maturation and addition of X-Glu, these pollen did not stain blue, nor did agrobacteria containing no GUS gene but the $KAN_{35S}$ gene after cocultivation with pollen and the addition of X-Glu. Pollen which were not infected with agrobacteria did not stain blue either after the addition of X-Glu.

Pollen from a $GUS_{35S}$-transformed plant (leaf-disk method), which served as a positive control, did stain blue. Another agrobacteria stain which did contain a functional $GUS_{35S}$ gene in the T-DNA but was impaired in its virulence function (binary vector without Ti plasmid) did not show GUS activity in the pollen.

An extract was prepared from a third portion of the pollen. For this purpose, portions of $4\times10^5$ pollen were collected by centrifugation and taken up in extraction buffer (6). The pollen was crushed open using glass beads and simultaneous ultrasound treatment. The fluorimetric GUS assay was carried out as described by Jefferson. 50 µl of extract were made up to 1 ml with extraction buffer, and MUG(4-methylumbelliferyl glucuronide) was added to a final concentration of 1 mM. Aliquots of 200 µl were withdrawn every 10 to 30 sec, and the enzyme reaction was stopped using 800 µl of $Na_2CO_3$ (0.2M). In a fluorimeter, the absorbance at 455 nm following excitation at 365 nm was measured, and the values were converted to concentrations in µM/ml with the aid of MUG standard solutions.

Enzyme activity of beta-glucuronidase from tobacco pollen extracts after co-culturing with *A tumefaciens*, measured by fluorimetry:

After 10, 20 and 30 minutes (∥M/ml):

|  | 10 min | 20 min | 30 min |
| --- | --- | --- | --- |
| Standard 1 | 1.0 | 1.0 | 1.0 |
| Standard 2 | 0.1 | 0.1 | 0.1 |
| Pollen without agrobacteria | 0.016 | 0.020 | 0.019 |
| Pollen, co-cultured with $GUS_{35S}$ agrobacteria | 0.057 | 0.078 | 0.109 |
| Pollen, co-cultured with $KAN_{35S}$ agrobacteria | 0.023 | 0.019 | 0.021 |
| Pollen with $GUS_{35S}$ with "binary vector", without Ti plasmid | 0.022 | 0.023 | 0.018 |
| Pollen from transgenic $GUS^+$ plant | 0.051 | 0.085 | 0.121 |

CULTURE MEDIA (1) AMGLU medium
Miller's macrosalts
MS microsalts
Sucrose (0.25M)
Glutamine (440 mg/l)
pH 7
(2) MR24 medium
MS macrosalts
MS microsalts
Sucrose (0.5M)
Glutamine (440 mg/l)
Coconut water (2% by volume)
Lactalbumin hydrolysate (200 mg/l)
Inositol (100 mg/l)
pH 7
(2') MR26 medium
Like MR24 medium, but lactalbumin hydrolysate (1 g/l)
(3) M1S medium
Miller's macrosalts
MS microsalts
FeEDTA ($10^{-1}$M)
Sucrose (0.25M)
pH 7
(3') M2S medium
Kyo and Harada's salts (in Planta, Vol. 186, pages 427–432 (1986))
Sucrose (0.25M)
pH 7
(4) Seed germination medium
MS macrosalts
MS microsalts
FeEDTA ($10^{-4}$M)
Sucrose (1% by weight)
Agar (0.8% by weight)
Kanamycin $SO_4$ (50 mg/l)
pH 5.5
(5) Calcium washing solution $CaCl_2 \times 2H_2O$ (0.16M)

MES buffer (0.5% by weight)

pH 5.6

(6) Extraction buffer $NaPO_4$ (50 mM, pH 7)

2-mercaptoethanol (10 mM)

$Na_2EDTA$ (10 mM)

Sodium lauroylsarcosinate (0.1%)

Triton X-100 (0.1%)

EXAMPLE 9

In Vitro Maturation of Microspores and in Vivo Pollination

After isolation, uninucleate microspores were first cultured for three days in medium T1 (0.5M sucrose, 3 mM glutamine, 10 mg/ml lactalbumin hydrolysate, 10 mM $KNO_3$, 1 mM $Ca(NO_3)_2.4H_2O$, 1 mM $MgSO_4.7H_2O$, 0.16 mM $H_3BO_3$, 1 mM uridine, 0.5 mM cytidine, 1 mM phosphate buffer, pH 7) which is a modification of the medium MR26. Then, the cultures were diluted with an equal amount of medium AMGLU (MS macro- and micro-salts, 0.5M sucrose, 3 mM glutamine) and after one more day finally diluted with an equal amount of Medium P (1.17M sucrose, 0.1M L-proline). In vitro matured microspores were allowed to germinate in medium GQ (0.3M sucrose, 1 g/l casein hydrolysate, 1 mM $KNO_3$, 0.3 mM $Ca(NO_3)_2.4H_2O$, 0.8 mM $MgSO_4.7H_2O$, 1.6 mM $H_3BO_3$, 2.5 mM MES (2-N-morpholinoethansulfonic-acid) at pH 5.9, 2 $\mu M$ quercetin). High germination frequencies were achieved. In microspore cultures 65% of the starting pollen population germinated after 7 h incubation in the extract-enriched medium GQ. For in vivo pollination, the in vivo matured pollen was washed several times in medium GQ and 3 $\mu l$ containing 5,000 to 10,000 pollen grains were placed on stigmas of emasculated flowers. The pollination droplet quickly dried on the surface, and after four weeks seed pods were produced which contained on average 200 to 300 seeds per pod. In some experiments, up to 1000 seeds were obtained per pod which is close to the number produced by normal in vivo self-pollination.

EXAMPLE 10

Transient Expression of the GUS-Reporter Gene in in vitro Matured Pollen

Experiments were performed to obtain a high transient microspore transformation frequency. Uninucleate microspores were bombarded immediately after isolation. The suspension (0.7 ml) containing $5 \times 10^5$ cells in medium B (150 mg/l KCl, 25 mg/l $MgSO_4.7H_2O$, 15 mg/l$CaCl_2.2H_2O$, 1 mM $KHPO_4$, 0.3M mannitol, pH 7) containing 24% polyethyleneglycol 6000, was distributed evenly on a sterile filter paper (Whatman No. 1) placed in a 10 cm Petri dish (Sterilin, UK). The holium driven PDS-1000/He particle delivery system (Bio-Rad, USA) was used for the biolistic transformation. Bombardment was performed essentially as described by Klein et al. (Nature 327:70–73, 1987). Plasmid-DNA was precipitated on gold particles with an average diameter of 1.1 $\mu m$. The coating reaction consisted of 25 $\mu l$ gold suspension (prepared in 60 mg/ml sterile water), 5 $\mu g$ DNA (in 10 mM Tris, 1 mM EDTA, pH 8), 25 $\mu l$ $CaCl_2$ (2.5M) and 10 $\mu l$ spermidine (0.1M, free base). DNA was precipitated on the microprojectiles within the same coating process (1:1 molar ratio, final DNA-concentration=7 $\mu g$). The suspension was vortexed for 5 min and was then incubated for at least 30 min at 4° C. After two washing steps in 96% ethanol (each centrifugation 1 min at 7,800 g) the pellet of the coated particles was resuspended in 21 $\mu l$ of 96% ethanol and sonicated briefly. Per bombardment, 7 $\mu l$ of the suspension was loaded onto a macrocarrier and dried under the laminar flow. Each transformation event included three bombardments. About 1% of GUS-positive pollen grains were routinely observed after two to three days of maturation and staining with X-gluc.

EXAMPLE 11

Transformed Seedlings after Pollination with in vitro Matured, Bombarded Microspores To produce transgenic plants, microspores were bombarded with the plasmid MIPHYG. Plasmid MIP contains the npt II gene of E. coli under control of the nos-promoter in order to select the seeds produced after pollination with the bombarded, in vitro matured pollen for kanamycin resistance. As a marker gene to identify more precisely the putative transformants, the hpt gene for hygromycin resistance was included in pMIP to result in plasmid MIPHYG. The second plasmid to be used for bombardment was pBI121 which also contained the npt II gene under control of the nos-promoter but the uid A gene as a reporter gene.

Microspores from 20 to 25 flowers were isolated to yield about 6 to 10 million microspores each. After bombardment and in vitro maturation, 3,000 to 12,000 seeds per experiment were obtained, in total 40,000 seeds. After germination of these seeds, five seedlings turned out to be kanamycin-resistant. This means that one transformant was found amongst 8,000 seeds.

A Southern blot using the complete npt II coding region as a probe confirmed that the five kanamycin-resistant F1-plants were transgenic. The npt II probe hybridized to DNA of all five, after digestion with Sal 1 and Pst I, producing bands of the same, expected size. The npt II probe was further hybridized to undigested DNA of the four transformants. Hybridization only occurred to the uncut chromosomal plant DNA, and no bands at shorter size were found indicating that the expressed transgene had integrated into chromosomal DNA of the tobacco plants.

Four of the five transformants (F1-plants) had been produced by bombardment with pMIPHYG while one transformant had been produced by bombardment with pBI121. Southern blot analysis, using as a probe the plasmid-specific genes hpt and uid A, respectively, revealed that indeed the four pMIPHYG-transformants contained the hpt-gene while the pBI121-transformant contained the uid A gene. In a border analysis the DNA of the four plants transformed with pMIPHYG was cut with Sal 1 which cuts only once in the vector, i.e. in the hpt gene, and was hybridized with the hpt gene as a probe. Indeed, fragments of a larger size than the hpt gene were produced and the size of these fragments differed from transformant to transformant. This finding makes it very unlikely that the transgenes were present in the plant as a self-replicating episome, either in plant cells or cells of an endophyte that may have been transformed accidentally.

In one plant, only one fragment hybridized to the hpt probe, indicating a simple integration pattern. Comparison with plasmid DNA in an amount to reconstruct integration of one or two plasmids, indicated that one or possibly two copies were integrated in this plant. In the other three plants, a more complex banding pattern was found. Probably several copies had integrated into the genome of these plants. Also with the pBI121-transformed plant a complex banding pattern was found.

To determine whether the transgenes in the five transformants are transmitted to the next generation and to finally exclude the possibility of transformation of an endophyte, a genetic analysis of the offspring was performed with F2-seeds produced by self pollination of the F1-plants and by back-crosses with wild-type plants. The F2-seeds were grown on kanamycin-containing plates and the number of kanamycin-resistant and kanamycin-sensitive seedlings was counted. Transgenic offspring were produced by all five transformed F1-plants, however, with different segregation patterns. One pMIPHYG-transformant, i.e., the one which revealed a simple integration pattern in the Southern blot, showed perfect Mendelian segregation for one npt II locus and another one had a segregation pattern which was intermediate between a single and a dual integration indicating that probably integration had occurred at two loci on the same chromosome. The other two pMIPHYG- and the one pBI121-transformants showed, in the different crosses, less kanamycin-resistant seedlings than expected for integration into one locus.

In addition, a genetic analysis on the basis of a GUS assay was performed with F2-seedlings of the F1-transformant that contained pBI121. The seedlings on the plate were wounded and X-gluc was added to the surface of the plate. The same segregation ratios for self pollination and back-crosses were found as in the kanamycin selection experiment with this transformant.

We claim:

1. A method for producing transgenic seeds, which comprises the steps of:
   a) isolating uninucleated microspores from anthers and removing tissue embedding the uninucleated microspores,
   b) culturing the isolated microspores in a nutrient solution,
   c) transferring foreign genetic material into the isolated microspores to obtain transformed microspores,
   d) maturing completely the transformed microspores to obtain transformed pollen grains in vitro,
   e) pollinating receiver plants with the transformed pollen grains and obtaining the transgenic seeds from the pollinated receiver plants.

2. The method according to claim 1, wherein the foreign genetic material is transferred into the isolated microspores biolistically using a DNA gun.

3. The method according to claim 1, wherein the foreign genetic material is transferred into the isolated microspores using Agrobacterium.

4. The method according to claim 1, wherein the foreign genetic material is transferred into the isolated microspores using microinjection.

5. The method according to claim 1, wherein the foreign genetic material is transferred into the isolated microspores using electroporation.

6. A transformed pollen grain produced by the method of claim 1.

7. A transgenic seed produced by the method of claim 1.

8. A transgenic plant derived from the transgenic seed of claim 7.

9. A method for producing transgenic plants, which comprises the steps of:
   a) isolating uninucleated microspores from anthers and removing tissue embedding the uninucleated microspores,
   b) culturing the isolated microspores in a nutrient solution,
   c) transferring foreign genetic material into the isolated microspores to obtain transformed microspores,
   d) maturing completely the transformed microspores to obtain transformed pollen grains in vitro,
   e) pollinating receiver plants with the transformed pollen grains and obtaining the transgenic seeds from the pollinated receiver plants
   f) growing the transgenic seeds to obtain the transgenic plants.

10. The method according to claim 9, wherein the foreign genetic material is transferred into the isolated microspores biolistically using a DNA gun.

11. The method according to claim 9, wherein the foreign genetic material is transferred into the isolated microspores using Agrobacterium.

12. The method according to claim 9, wherein the foreign genetic material is transferred into the isolated microspores using microinjection.

13. The method according to claim 9, wherein the foreign genetic material is transferred into the isolated microspores using electroporation.

14. A transgenic plant produced by the method of claim 9.

15. An in vitro transformed and matured pollen grain.

16. A progeny of the pollen grain of claim 15.

17. A trangenic seed derived from the pollen grain of claim 15.

18. A trangenic plant derived from the transgenic seed of claim 17.

19. A trangenic seed derived from the progeny of claim 16.

* * * * *